United States Patent [19]

Anderson et al.

[11] Patent Number: 5,210,238
[45] Date of Patent: May 11, 1993

[54] PERFLUORINATED CYCLIC HEMIKETALS, CORRESPONDING PERFLUORODIKETONES AND PROCESS FOR PREPARING THEM

[75] Inventors: John D. Anderson, South Augusta, Ga.; Darryl D. Desmarteau, Clemson, S.C.; Walter Navarrini, Milan, Italy

[73] Assignee: Ausimont S.p.A., Milan, Italy

[21] Appl. No.: 824,072

[22] Filed: Jan. 23, 1992

[51] Int. Cl.$^5$ .................. C07D 309/10; C07D 307/20
[52] U.S. Cl. .................................. 549/417; 549/476
[58] Field of Search ........................... 549/417, 476

[56] References Cited

U.S. PATENT DOCUMENTS

| | | | |
|---|---|---|---|
| 2,515,304 | 7/1950 | Jones | 549/476 |
| 2,920,081 | 1/1960 | Privette et al. | 549/476 |
| 3,029,252 | 4/1962 | Simmons, Jr. | |
| 3,185,734 | 5/1965 | Fawcett et al. | |
| 3,379,765 | 4/1968 | Anello et al. | |

FOREIGN PATENT DOCUMENTS

| | | |
|---|---|---|
| 3032471 | 3/1981 | Fed. Rep. of Germany |
| 2058763A | 8/1980 | United Kingdom |

OTHER PUBLICATIONS

L. S. Chen and G. J. Chen, Journal of Fluorine Chemistry 42, 371–387 (1989).
J. Am. Chem. Soc. 91, 1310 (1969).
Tetrahedron Letters, 25, 2195–2198 (1984).
J. Am. Chem. Soc. 112, 7619 (1990).

*Primary Examiner*—Nicky Chan
*Attorney, Agent, or Firm*—Bryan Cave

[57] ABSTRACT

Perfluorinated cyclic hemiketals of formula:

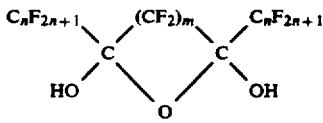

where $n=1-6$, $m=2-3$, and their corresponding perfluoridiketones. The latter are prepared by means of perfluoroalkylation reaction of diacyl fluorides with perfluoroalkyl-trialkyl silanes. The perfluorodiketones can be then reacted with $H_2O$ in order to obtain said cyclic hemiketals.

3 Claims, No Drawings

PERFLUORINATED CYCLIC HEMIKETALS, CORRESPONDING PERFLUORODIKETONES AND PROCESS FOR PREPARING THEM

The present invention relates to perfluorinated cyclic hemiketals, to the corresponding perfluorodiketones and to a process for preparing them.

Patent application EP-A-330,058 describes a process for transferring perfluoroalkyl radicals onto carbonyl substrates (aldehydes or ketones) by reacting the latter with a perfluoroalkyl-trimethyl silane, using an alkali metal fluoride as a catalyst. From such reaction, a silyl ether is obtained, which, by hydrolysis, provides the corresponding alcohol.

The process is utilizable only on hydrogenated or partially fluorinated substrates.

The Applicant has now surprisingly found that the perfluoroalkylation reaction with perfluoroalkyl-trialkyl silanes can be conducted on perfluoro-diacyl fluorides, with production of new perfluorodiketones, and that these diketones react with water to form surprisingly stable new cyclic hemiketals.

Thus, an object of the present invention are the perfluorinated cyclic hemiketals of formula:

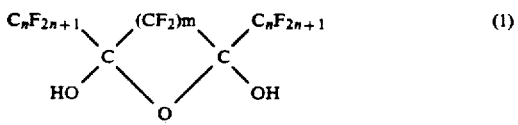

where n is an integer from 1 to 6, m is 2 or 3.

A second object of the present invention are the perfluorodiketones of formula:

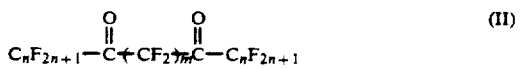

where n is an integer from 1 to 6, m is 2 or 3.

A third object of the present invention is a process for preparing the perfluorodiketones of formula (II), which consists in reacting a perfluoro-diacyl fluoride of formula:

with a perfluoroalkyl-trialkyl silane of formula:

where R is an alkyl having 1 to 4 carbon atoms, in the presence of an alkali metal or quaternary ammonium fluoride MF, in an anhydrous aprotic polar solvent.

Still a further object of the present invention is represented by a process for preparing the cyclic hemiketals of formula (I), which consists in reacting the corresponding perfluorodiketone of formula (II) with $H_2O$.

In formulas (I) and (II) n is preferably an integer from 1 to 4, more preferably it is 1 or 2.

The diacyl fluorides of formula (III) are known products and are preparable, for example, according to what is described in J.Am.Chem.Soc., 91, 1310 (1969) or in patent DE-3,032,471.

Also the perfluoroalkyl-trialkyl silanes of formula (IV) are known in themselves and can be prepared according to the methods described in the already cited patent application EP-A-330,058 or in Tetrahedron Letters, 25, 2195-2198 (1984).

Fluoride MF is, for example, a Na, K, Cs or Rb fluoride. Preferably it is KF.

As an alternative, it is possible to utilize a tetraalkyl ammonium fluoride, provided it is soluble enough in the solvent utilized as a reaction medium. An example is represented by the tetramethyl ammonium fluoride, which is preparable for example according to what is described in J.Am.Chem.Soc., 112, 7619 (1990).

As already mentioned above, the reaction is carried out in an anhydrous aprotic polar solvent. Any solvent of this type is suitable, provided that fluoride MF is at least partially soluble in it. There are utilizable, for example, the nitriles, such as acetonitrile and benzonitrile, the ethers, such as diethylether, dioxane, tetrahydrofuran, glymes (e.g. 2-methoxyethylether), or mixtures thereof.

Preferably the reaction is effected in benzonitrile.

The reaction temperature is usually maintained approximately from −45° to +45° C., preferably from −15° to +25° C., approximately.

The pressure is not a critical parameter. The reaction is generally conducted at atmospheric or subatmospheric pressure, but, if necessary, pressures ranging from 1 to 10 atm. can be employed.

As regards the reagents, the perfluoroalkyl-trialkyl silane/diacyl fluoride molar ratio generally ranges from 2.0:1.0 to 4.0:1.0, preferably from 2.0:1.0 to 2.6:1.0, while the fluoride MF/perfluoroalkyl-trialkyl silane molar ratio generally ranges from 1.0:1.0 to 4.0:1.0, preferably from 1.0:1.0 to 1.8:1.0.

On conclusion of the reaction, the diketone can be isolated by suction by means of a vacuum pump, under slight heating of the solid obtained as a reaction product. Generally, a mild heating to a temperature in the range of from 50° to 90° C. is sufficient.

The resulting diketone can be reacted with $H_2O$ in order to prepare the cyclic hemiketal. Such reaction does not require particular conditions: the diketone promptly reacts with water at temperatures around room temperature, i.e., for example, from 10° to 50° C.

As an alternative, the reaction with water can be effected in situ, i.e. without separating the diketone from the reaction mixture obtained in consequence of the perfluoroalkylation. The same reaction conditions specified hereinabove are employable.

The perfluorinated cyclic hemiketals of the present invention can be utilized as monomers in polycondensation reactions for the synthesis of fluorinated polymers (polyurethanes, polyesters, etc.).

The perfluorodiketones are useful as solvents and as intermediates for the synthesis of the abovesaid hemiketals, as already described herein.

The following examples are given for illustrative purposes and are by no way to be considered as a limitation of the scope of the present invention.

EXAMPLE 1

Into a reactor consisting of a Pyrex ® 250 ml flask, a magnetic stirrer, inlet and outlet connections connected with a vacuum line and a line for the inlet of liquids, there were introduced 0.77 g (13.0 mmols) of KF, which had been previously molten and ground, in a nitrogen atmosphere.

The reactor was then evacuated and 3.0 ml of anhydrous benzonitrile were introduced thereinto by injection through the inlet line for liquids. From the reactor, cooled to $-196°$ C. with liquid nitrogen, the residual traces of air were sucked. Into the reactor there were transferred under vacuum and condensed 2.99 mmols of perfluoroglutaryl fluoride FOC-$(CF_2)_3$-COF and 6.33 mmols of $(CH_3)_3Si$—$CF_3$. The reactor was gradually heated to $0°$ C. by immersion into a water-ice bath.

Stirring was started as soon as the reaction mixture was molten (m.p. of $C_6H_5CN = -13°$ C.). The reactor was gradually brought from $0°$ to $20°$ C. After a 17-hour stirring, the volatile matters were removed by suction through the vacuum line (45 minutes at $23°$ C.): no presence of diketone was observed in the recovered products. The reactor was then heated to about $70°$ C. and suction was carried on for 2 hours. 2.41 mmols of $CF_3CO$—$(CF_2)_3$—$COCF_3$ were obtained (yield: 80.7%, based on FOC—$(CF_2)_3$—COF).

The obtained product was characterized through the IR, $^{19}$F-NMR and mass spectra:

IR: position and intensity of the main bands (m=medium, vs=very strong, w=weak) (p=2 torr.): 1790 (sharp, m), 1249 (vs), 1194 (vs), 1013 (m), 910 (m), 842 (m), 732 (m), 642 (w) [cm$^{-1}$].

$^{19}$F-NMR: $CF_3{}^ACOCF_2{}^BCF_2{}^CCF_2{}^BCOCF_3{}^A$ (CDCl$_3$, $20°$ C.): A $-75,1$ (6F), B $-118,1$ (4F), C $-121,8$ (2F).

MASS SPECTRUM: main peaks: EI: 247 (M—COCF$_3$)$^+$, 197 (M—CF$_2$COCF$_3$)$^+$, 147 (CF$_3$COCF$_2$)$^+$, 100 (CF$_2$CF$_2$)$^+$, 97 (CF$_3$CO)$^+$, 69 (CF$_3$)$^+$, 50 (CF$_2$)$^+$; CI: 345 (MH)$^+$, 247 (MH—H—COCF$_3$)$^+$, 231 (MH—H—O—COCF$_3$)$^+$, 131 (MH—H—O—CF$_2$CF$_2$COCF$_3$)$^+$, 100 (CF$_2$CF$_2$)$^+$.

The boiling point, determined according to the Sivoloboff method, was $78°$ C. /750 mm Hg.

EXAMPLE 2

Utilizing the same reactor and following the same modalities described in example 1, 0.84 g (14 mmols) of KF were introduced into the reactor. The reactor was evacuated. 2.5 ml of anhydrous benzonitrile were injected through the inlet line for liquids. After cooling to $-196°$ C., the residual air traces were sucked.

Through the vacuum line, 3.03 mmols of perfluorosuccinyl fluoride FOC—$(CF_2)_2$—COF and 6.50 mmols of $(CH_3)_3Si$—$CF_3$ were introduced into the reactor and condensed. The reactor was gradually heated to $0°$ C. in a water-ice bath and stirring was started. The temperature was then gradually brought to $20°$ C. (18 hours). The volatile matters were removed by means of suction (45 minutes at $23°$ C.). No presence of diketone was observed in the recovered products.

Suction was continued for 1.5 hours while heating the reactor to about $70°$ C. 1.60 mmols of $CF_3CO$—$(CF_2)_2$—$COCF_3$ were obtained. (Yield: 52.8%, based on FOC—$(CF_2)_2$—COF).

The obtained product was characterized through the IR and $^{19}$F-NMR spectra:

IR: position and intensity of the main bands (m=medium, s=strong, vs=very strong, w=weak) (p=4 torr.): 1785 (sharp, m), 1311 (s), 1287 (vs), 1246 (vs), 1200 (vs), 1090 (m), 1050 (m), 909 (m), 842 (s), 724 (vs) [cm$^{-1}$]. $^{19}$F-NMR: $CF_3{}^ACOCF_2{}^BCF_2{}^BCOCF_3{}^A$ (CDCL$_3$, $20°$ C.): A $-75,1$ (6F), B $-119,5$ (4F).

The boiling point, determined according to the Sivoloboff method, was equal to $59°$-$61°$ C./742 mm Hg.

EXAMPLE 3

9 μl of H$_2$O (0.50 mmols) were injected into a 50 ml flask equipped with inlet and outlet connections connected with a vacuum line. The flask was cooled to $-196°$ C. with liquid nitrogen and evacuated. Through the vacuum line, 0.56 mmols of $CF_3CO$—$(CF_2)_3$—$COCF_3$ were condensed in the flask. The flask was allowed to heat up to room temperature.

A white solid product of formula:

$$\begin{array}{c} CF_2 \\ CF_2 \quad CF_2 \\ | \quad \quad | \\ CF_3-C \quad \quad C-CF_3 \\ HO \quad O \quad OH \end{array}$$

was obtained; the yield was nearly quantitative.

The obtained product was characterized through IR and $^{19}F$—NMR spectra:

IR: position and intensity of the main bands (m=medium, s=strong, vs=very strong, w=weak): 3568 (m), 3252 (broad, m), 1654 (broad, w), 1637 (broad, w) 1301 (sharp, m), 1253 (s), 1234 (s), 1187 (s), 1161 (s), 1062 (s), 919 (s), 837 (m), 744 (m), 684 (m), 646 (w), 629 (w) [cm$^{-1}$].

$^{19}$F-NMR: $CF_3{}^AC'OHO'CF_2{}^BCF_2{}^CCF_2{}^BC'OHCF_3{}^A$ (CD$_3$CN, $20°$ C): A $-80,0$ (6F'), B $-126,5;-129,8$ (4F, AB patt J$_{AB}=266,6$ Hz, v$_o$d$=631,8$ Hz), C $-119,3;-140,5$ (2F, AB patt J$_{AB}=275,2$ Hz, v$_o$d$=3978,6$ Hz)).

The melting point was equal to $61°$-$63°$ C.

EXAMPLE 4

Following the same procedure described in example 3, 9 μl of H$_2$O (0.50 mmols) were reacted with 0.53 mmols of $CF_3CO$—$(CF_2)_2$—$COCF_3$.

A white solid product of formula:

$$\begin{array}{c} CF_2-CF_2 \\ / \quad \quad \backslash \\ CF_3-C \quad \quad C-CF_3 \\ HO \quad O \quad OH \end{array}$$

was obtained; the yield was nearly quantitative.

The obtained product was characterized through IR and $^{19}$F-NMR spectra:

IR: position and intensity of the main bands (m=medium, s=strong, vs=very strong, w=weak): 3656 (m), 3578 (m), 3223 (broad, m), 1612 (broad,w), 1326 (m), 1217 (vs), 1170 (s), 1130 (m), 1030 (s), 943 (m), 860 (m), 763 (w), 743 (m), 710 (w) [cm$^{-1}$].

$^{19}$F-NMR: $CF_3{}^AC'OHO'CF_2{}^BCF_2{}^CCF_2{}^BC'OHCF_3{}^A$ (CD$_3$CN, $20°$ C.): it is a mixture of diastereoisomers.

Diastereoisomer 1 (60%): A $-80.3$ (6F), B $-120.6;-132.1$ (4F, AB patt J$_{AB}=246.3$ Hz).

Diastereoisomer 2 (40%): A $-79.9$ (6F), B $-126.0;-130.2$ (4F, AB patt J$_{AB}=244.0$ Hz).

What is claimed is:

1. Perfluorinated cyclic hemiketal of formula:

$$\begin{array}{c} C_nF_{2n+1} \quad (CF_2)_m \quad C_nF_{2n+1} \\ \backslash \quad / \quad \backslash \quad / \\ C \quad \quad C \\ / \quad \backslash \quad / \quad \backslash \\ HO \quad O \quad OH \end{array} \quad (I)$$

where n is an integer ranging from 1 to 6, m is 2 or 3.

2. The perfluorinated cyclic hemiketal of claim 1, wherein n=1 and m=3.

3. The perfluorinated cyclic hemiketal of claim 1, wherein n=1 and m=2.

* * * * *